US00PP27451P2

(12) United States Plant Patent
Mortensen

(10) Patent No.: US PP27,451 P2
(45) Date of Patent: Dec. 13, 2016

(54) GRAPEVINE PLANT NAMED 'BN5-4'

(50) Latin Name: ***Vitis* sp.**
Varietal Denomination: BN5-4

(71) Applicant: Florida Foundation Seed Producers, Inc., Marianna, FL (US)

(72) Inventor: John Mortensen, Marianna, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 4 days.

(21) Appl. No.: 14/545,468

(22) Filed: May 7, 2015

(51) Int. Cl.
*A01H 5/08* (2006.01)

(52) U.S. Cl.
USPC ..... Plt./205

(58) Field of Classification Search
USPC ..... Plt./205
See application file for complete search history.

(56) References Cited

PUBLICATIONS

Pool et al., "Remaily seedless grape," New York's Food and Life Sciences Bulletin, No. 89, 1981.
Li et al., "PR-1 gene family of grapevine: a uniquely duplicated PR-1 gene from a *Vitis* interspecific hybrid confers high level resistance to bacterial disease in transgenic tobacco," Plant Cell Reports 30(1):1-11, 2011.

*Primary Examiner* — Annette Para
(74) *Attorney, Agent, or Firm* — Dentons US LLP

(57) ABSTRACT

A new and distinct hybrid wine grapevine plant named 'BN5-4', characterized by the following unique combination of characteristics: Very vigorous with extremely high disease resistance in the southeastern United States, including resistance to bacterial Pierce's disease and a host of fungal diseases. Average- to high-yielding vines, with dark, purple-skinned, seeded berries. Wine from the variety may be produced to be light red with a pleasant character and low residual sugar, or with a foxy character.

4 Drawing Sheets

STATEMENT REGARDING FEDERALLY SPONSORED RESEARCH

This invention was made with government support awarded by the Cooperative State Research, Education, and Extension Service, USDA. The government has certain rights in this invention.

Latin name of the genus and species of the plant claimed: *Vitis* sp.

Variety denomination: 'BN5-4'.

BACKGROUND OF THE INVENTION

The present invention relates to a new and distinct variety of grapevine named 'BN5-4'. 'BN5-4' produces dark-purple-colored grape berries on bunches for use in wine production. 'BN5-4' originated in 1987 as a selected seedling from a controlled cross between a native *Vitis aestivalis* vine (female parent) pollinated with the self-fertile *Vitis* interspecific hybrid cultivar 'Remaily Seedless' (male parent). The seedling plant originally was named 'BN5-4' because it was the fourth seedling in the fifth row of "BN" block, which was located in Leesburg, Fla. The seedling plant was vegetatively propagated by cuttings to create several hundred identical clone plants for further evaluation. 'BN5-4' was continuously grown at the Leesburg, Fla. site until it closed in 1990. 'BN5-4' then was re-established for further evaluation in Apopka, Fla. Evaluation of 'BN5-4' in the field for more than 25 years has confirmed the vine to be reliably vigorous and resistant to bacterial Pierce's disease, as well as a host of fungal diseases. 'BN5-4' is susceptible to Phylloxera, a leaf-gall-inducing insect, although leaf galling does not noticeably affect growth, performance, or durability.

'BN5-4' was first asexually reproduced in 1988 by cuttings in Leesburg, Fla. Asexual reproduction of 'BN5-4' by dormant and green cuttings shows that the foregoing and all other characteristics and distinctions remain true to form and are established and transmitted through succeeding propagations.

SUMMARY OF THE INVENTION

The present invention relates to a new and distinct interspecific hybrid grapevine variety, which will hereinafter be denominated as 'BN5-4', and more particularly as a self-fertile grapevine that is remarkably vigorous and disease resistant in the sub-tropical Floridian environment. The new Florida Hybrid Bunch Grape (FHBG) variety, 'BN5-4', is distinguished from all other grape varieties by the following unique combination of characteristics: vigorous growth in a humid, sub-tropical environment, exemplary resistance to the endemic bacterial pathogen *Xylella fastidiosa*, the causal agent of Pierce's disease, exemplary resistance to a host of fungal diseases endemic to the humid sub-tropical environment, and ability of the fruit to produce an acceptable dry light red wine. Evaluation of wine quality from 'BN5-4' has reached mixed conclusions, ranging from good-to-poor, depending on harvest time and fermentation methods. Under best practices, the wine produced by 'BN5-4' is lightly red-pigmented and can be finished dry, with little residual sugar.

Female parent *Vitis aestivalis* is a vigorous female vine native to Florida that produces small purplish berries, and male parent 'Remaily Seedless' is a self-fertile, green-berried, seedless variety developed at Cornell University in 1981. 'BN5-4' is distinct from the female parent by being self-fertile, having leaves without deep sinuses, and with larger fruit clusters. 'BN5-4' differs from the male parent by having purple berries and possessing seeds.

BRIEF DESCRIPTION OF THE DRAWINGS

'BN5-4' is illustrated by the accompanying photographs, which show the vine's from, foliage, and fruit. The colors shown are as true as can be reasonably obtained by conventional photographic procedures. The colors (except those in common terms) are described from R. H. S. Colour Chart published by The Royal Horticultural Society in London (second edition), in association with the Flower Council of Holland.

DETAILED BOTANICAL DESCRIPTION

Phenotypic Description of *Vitis* sp. 'BN5-4'

Figure 1:
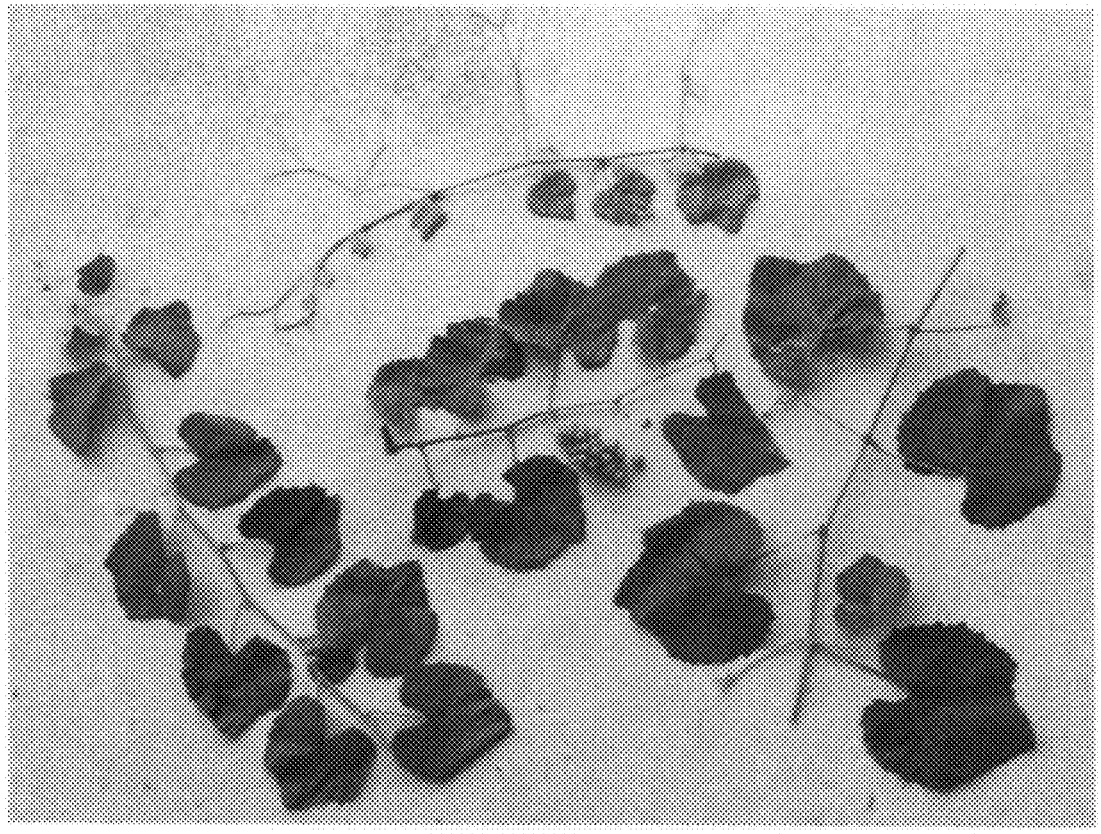
FIG. 1—Shows the typical vegetative morphology of stems, leaves and tendrils.
Figure 2:
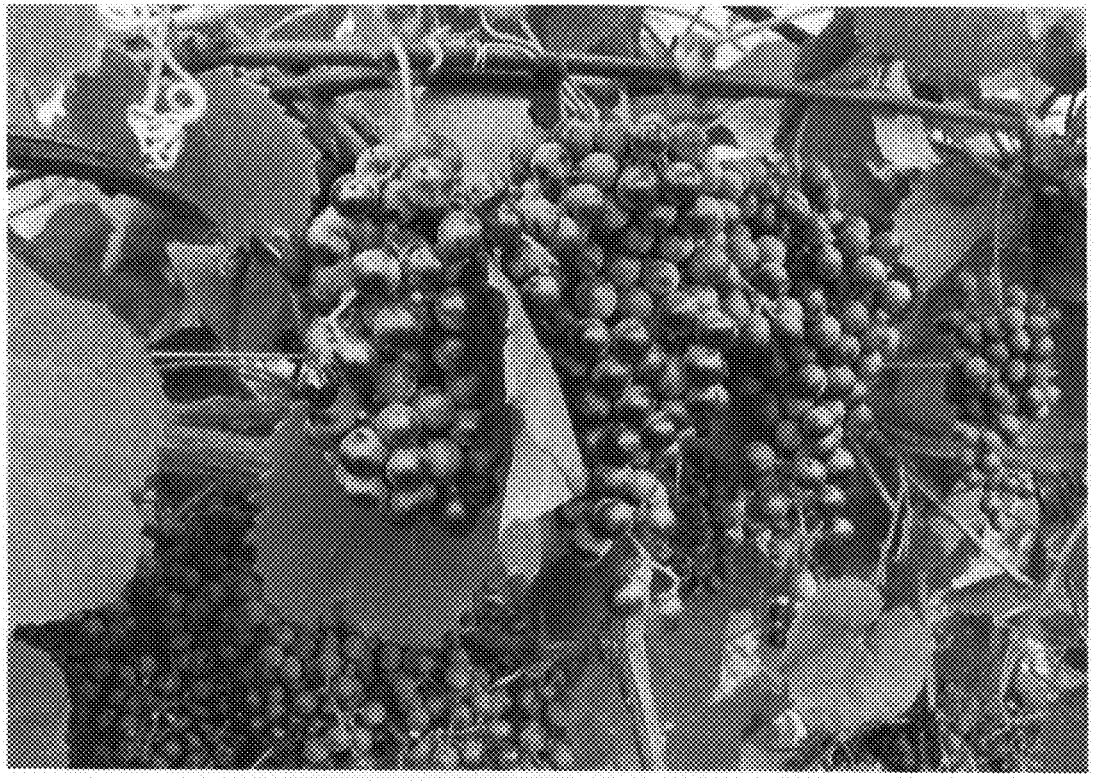
FIG. 2—Shows the typical arrangement of ripe fruit on the vine.
Figure 3:
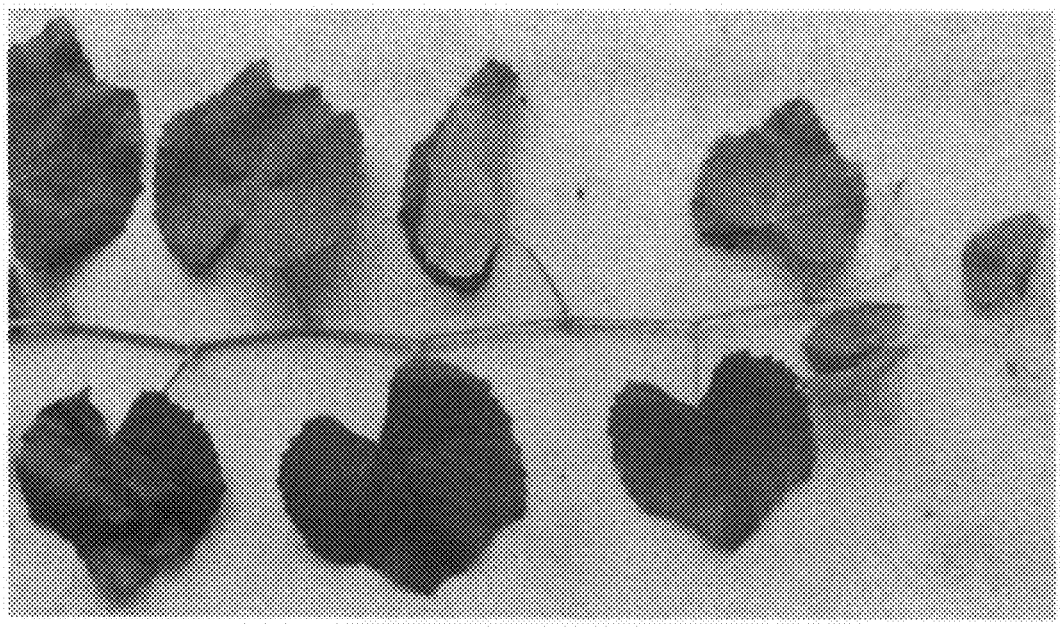
FIG. 3—Shows a typical shoot demonstrating leaf morphology and distribution.
Figure 4:
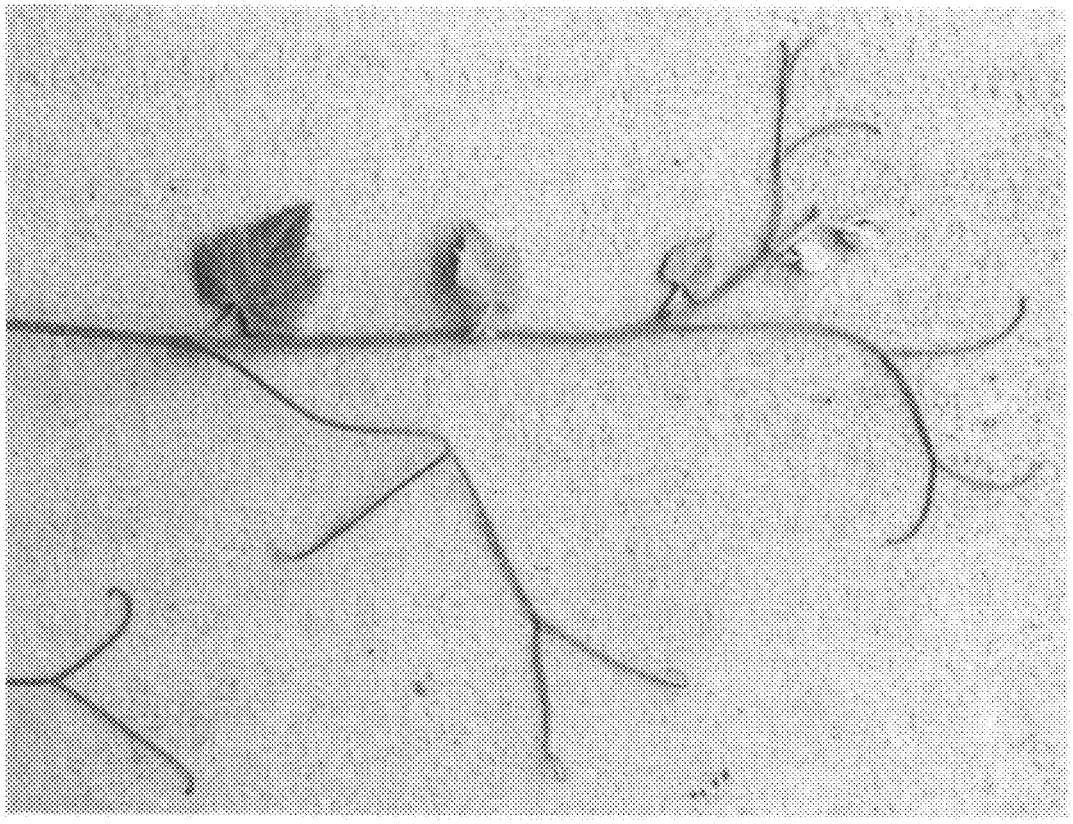
FIG. 4—Shows a shoot tip demonstrating shape, pigmentation, and pubescence of young leaves, and the trifurcate morphology of the tendrils.

Classification:

*Botanical.*—*Vitis* sp.

*Common name.*—Bunch grape.

Parentage:

*Female parent.*—*Vitis aesstivalis* Native female (unpatented).

*Male parent.*—*Vitis* 'Remaily Seedless' (unpatented).

Vine:

*Size.*—Medium.

*Vigor.*—High vigor.

*Density.*—Dense foliage.

*Productivity.*—Average.

*Yield.*—Approximately 14.5 kg (32 lb) per vine.

*Crop load.*—Approximately 0.6 kg (1.3 lb) per vine (weight of fruit per fresh pruning weight).

*Regularity of bearing.*—Regular.

*Root stock.*—Not applicable.

*Own root.*—Yes.

Trunk:

*Shape.*—Circular, thick, and straight.

*Diameter.*—Approximately 11.4 cm (4.5 in) measured on six-year-old vines at 1 m (39.37 in) above the vineyard floor.

*Surface texture.*—Shaggy.

*Surface appearance.*—Vertically striated.

*Inner bark color.*—Near Grey Purple (RHS N186C).

*Outer bark color.*—Near Grey Brown (RHS N200D).

Shoots:

*Young shoot.*—Date of bud break: Approximately March 15 in Apopka, Fla., although somewhat variable due to temperature fluctuation. Orientation: Upright. Form of tip: Open. Shape: Straight to slightly curved. Diameter: 9 mm (0.35 in) at base, 6 mm (0.24 inches) at midpoint, and 3 mm (0.12 in) at tip, as measured on shoots 70 cm (27.56 in) long. Surface texture: Hirsute due to an indument composed of simple trichomes. Density of simple trichomes: Dense, elongated, prostrate, near. Color of simple trichomes: White (RHS NN155B). Density of erect trichomes on tip: None. Texture of shoot surface beneath trichomes: Glabrous, near. Color of shoot surface beneath trichomes: Green (RHS 137A). Texture of bud scales at base of young shoot: Dried, near. Color of bud scales at base of young shoot: Grey-brown group (RHS N199B).

*Woody shoot* (*mature canes*).—Position: Recumbent. Shape: Slender. Cross section: Circular. Length: Approximately 5.5 m (216 in) at véraison. Diameter internode: Base: 13 mm (0.51 in). Midpoint: 9 mm (0.35 in). Tip: 3 mm (0.12 in). Diameter node: Base: 16 mm (0.63 in). Midpoint: 12 mm (0.47 in). Tip: 3.5 mm (0.14 in). Internode length: Base: 11 cm (4.33 in). Midpoint: 21.6 cm (8.50 in). Tip: 5.5 cm (2.15 in). Surface texture: Smooth with slightly raised parallel striations. Color of internodes: Near red group 46A on sunward surface and Near green group 137A on non-sun facing surfaces. A sparse buff-colored (Orange-White group 159A) tomentum composed of simple elongate trichomes evident within 120 cm of base, becoming increasingly dense acropetally. Color of nodes: Brown at base, becoming green with a ring of brown color typically developing on the acropetal side, becoming green at the tip. Density and color of trichomes on internodes: Elongate pale brown recumbent simple trichomes in thin patches on ventral surfaces of mature cane base becoming increasingly dense toward the tip. Density of trichomes on nodes: Similar to internodes in position. Lenticels: Absent. Average length of canes: 548 cm (216 in).

*Tendrils.*—Young shoots first appear at eighth node from tip, however on young shoots that initiate in late season, tendrils appear at the second node. Young shoots: Alternate, bifurcate-to-trifurcate and ventrally curled at distal tips. Young shoots: Trichomes hirsute due to abundant elongated near; White NN155B trichomes. Mature shoots: Alternate at most nodes, approximately 27 cm long, reddish (red group 46A) and bifurcate-to-trifurcate, with first trifurcate branch approximately 10-cm long, occurring at approximately 15 cm distal to the tendril base. Mature shoots: Distal bifurcated tendril branches approximately 6-cm long, the branch occurring approximately 2.2 cm distal to the tendril base, ventrally recurved at distal tips. The bifurcate branch of some tendrils rarely convert to incomplete inflorescences.

*Dormant bud.*—Number: Average of 24 on a current single-season growth cane. Type: Compound bud or eye. Size (Width): Base: 7.5 mm (0.3 in). Midpoint: 5 mm (0.2 in). Tip: 3.5 mm (0.14 in).

Leaves:

*General.*—Arrangement on shoot: Simple and alternate. Shape: Orbicular. Lobe number: None.

*Young leaves* (*first distal* 4 *unfolded leaves*).—Shape: Concave. Size: Average 2 cm in length and 1.5 cm wide. Adaxial surface color: Color of surface minus dentations due to thick tomentum of prostrate trichomes, Near white group NN155A. Abaxial surface color: Near white group NN155A. Color of dentations (which lack tomentum): Near green group 135B. Anthocyanin coloration: Variable, typically on intermediary mat of trichomes on petioles and basipetal leaf veins near red-purple group 67A. Density of tomentum: Dense composed of simple prostrate trichomes.

*Mature leaf.*—Average length: Leaf, including petiole: Approximately 36 cm (14 in). Blade: Approximately 18.4 cm (7.3 in). Average width: Blade: Approximately 21.6 cm (8.5 in). Mid vein (L1): Approximately 17.8 cm (7 in) long. Second vein (L2): Approximately 14 cm (5.5 in). Third vein (L3): Approximately 11.4 cm (4.5 in). Adaxial surface: Color: Near medium green group 137A. Surface texture: Undulate, rugose. Surface appearance: Dull. Glossiness: Weak. Pubescence: Absent. Abaxial surface: Color: Near light green group 137C. Anthocyanin coloration on main veins: Variable; absent to near red-purple group 61A at basipetal vein surfaces. Surface texture: Undulate, rugose. Surface appearance: Dull. Glossiness: Absent. Pubescence: Nearly inconspicuous simple trichomes in small patches on veins. Leaf margin: Serrate-to-doubly senate with medium-sized, wedge-shaped, apiculate teeth.

*Petiole.*—Sinus: Shallow with small lobes. Length: Approximately 17.6 cm (6.9 in). Diameter: Approximately 4.5 mm (0.018 in) basipetally reducing to 3 mm (0.12 in) acropetally. Color: Variable; light green becoming near red-purple group 61A in central part, to near red-purple group N77C in the sun, increasing with maturity.

*Buds.*—Shape: Conical. Size: Medium, approximately 4 mm×6 mm. Position: Slightly held out. Cane bud fruitfulness: Basal most fruitful at 4th and 5th nodes. Time of bud burst: Approximately March 15 in Apopka, Fla. Texture and color of bud scales at base of young shoot: Dried, near grey-brown group N199B.

Flowers and flower buds:

*General.*—Inflorescence type: Panicle. Cluster at emergence: Orientation: Upright. Size: Generally small to medium. Length: Approximately 9 cm (3.54 in) Width: Approximately 6 cm (3.36 in). Peduncle length: Approximately 5 cm (2 in). Cluster at bloom: Orientation: Recumbent. Shape of cluster: Conical with distinct shoulders. Length: Approximately 23 cm (9 in). Width: Approximately 15 cm. (6 in). Structure: Typically bifurcate, with the branch point approximately 7 cm (2.8 in) distal. The minor branch approximately 8 cm (3.1 in) long with two secondary adjacent branches 4 cm (1.6 in) from proximal attachment. The main branch approximately 18 cm (7 in) long with 12 variously arranged opposite and alternate branches that are approximately 2.5-cm long at basipetal positions to 2-cm long distally.

*Flowers.*—Sex: Hermaphroditic. Number: Approximately 200, but highly variable in number. Size unopened: Diameter: Approximately 1 mm (0.4 in). Length: Approximately 2.5 mm (0.098 in). Surface texture: Smooth. Date of full bloom: Approximately April 5 at 75%. Calyptra color: Near green group 135B. Receptacle color: Near green group 135C. Stamens: Six and upright. Pistils: Well-developed, approximately 2.4-mm (0.09 in) long, near green group 135B. Pollen: Normal, fertile, abundant.

Fruit:

*General.*—Ripening period: Early, approximately June 25-July 15. Use: Wine. Keeping quality: Unknown. Shipping quality: Unknown. Date of first harvest: June 25. Solids sugar: Medium to high. Refractometer test: 21 soluble solids (sugar). Acid: 0.8. Juice pH: 3.4. Tendency to crack: None. Sensitivity to sunburn: Low. Fruit shrivel after ripe: Average to High. Secondary cluster: Yes.

*Cluster.*—Size: On spur pruned vines, the characteristics of fruit clusters are as follows: Length: Approximately 15.0 cm (5.91 in). Width: Approximately 10 cm (3.94 in). Shape: Conical. Density: Relatively dense approximately 120 berries per cluster on average. Clusters per vine: Approximately 39 when spur pruned. Clusters per shoot: Approximately 2-3.

*Peduncle.*—Length: Approximately 4 cm (1.6 in). Diameter: Approximately 2 mm (0.08 in). Color: Near group 46A proximally, changing to near green group 140B distally. Texture: Somewhat rough and hirsute.

*Pedicel.*—Attachment to berry: Good. Length: Approximately 5 mm (0.12 in). Diameter: Approximately 1.5 mm (0.59 in). Texture: Rough. Brush length: Approximately 2 mm (0.08 in).

*Berry.*—General use: Wine production. Ripening time: Approximately the second week of August in Apopka, Fla. Flowering and fruit set are somewhat indeterminate, so that unripe clusters typically are present as late as October, unless removed by thinning. Uniformity of size: Uniform. Size: Small. Berry weight: Average weight is approximately 1.4 g (0.05 oz). Shape: Round to slightly ovoid. Presence of seeds: Cross section: Round. Length: Approximately 14 mm (0.55 in). Width: Approximately 9 mm (0.35 in).

Skin:

*Thickness.*—Relatively thick.

*Texture.*—Smooth.

*Color.*—Near greyed-purple group N186A.

*Tenacity.*—Non-adherent and slips readily from flesh.

*Skin tendency to crack.*—None.

Flesh:

*Color.*—Translucent near yellow-green 145D.

*Texture.*—Firm.

*Juice production.*—Good.

*Color of juice.*—Near red-purple group 67A.

*Flavor.*—Sweet and fruity.

*Soluble solids.*—18.8% to 25% depending on time of harvest.

*Titratable acid.*—Approximately 0.8 to 1.5 from fruit harvested at approximately 18% soluble solids.

*Aroma.*—Neutral to slightly "foxy" aroma.

*Ripening.*—Uniform within clusters.

Seeds:

*Character of seeds.*—Prominent with approximately 3.6 per berry.

*Average weight* (100 *seeds*).—3.7 g (0.13 oz).

*Flesh to seed ratio.*—11:1.

*Seed color.*—Near greyed-orange group 177B.

*Seed shape and size.*—Pyriform shape and medium size.

Use:

*Primary use*.—Wine.

*Keeping quality*.—Average for wine grapes.

*Shipping and handling qualities*.—Unknown.

Resistance to disease:

*Bacterial disease resistance*.—Tolerant to Pierce's disease and does not exhibit symptoms.

*Fungal disease resistance*.—Highly resistant to all debilitating fungal diseases in the Floridian environment.

*Insect resistance*.—Susceptible to grape phylloxera (*Daktulosphaira vitifoliae* Fitch), which causes elongated cylindrical galls on leaves, but which does not inhibit growth and requires no control.

What is claimed is:

1. A new and distinct grapevine plant substantially as illustrated and described herein, characterized by high vigor and durability in the Floridian environment with use for production of red wine.

* * * * *